(12) United States Patent
Muraishi

(10) Patent No.: US 7,838,301 B2
(45) Date of Patent: Nov. 23, 2010

(54) METHOD AND APPARATUS FOR ASSAY IN UTILIZING ATTENUATED TOTAL REFLECTION

(75) Inventor: Katsuaki Muraishi, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 425 days.

(21) Appl. No.: 11/508,936

(22) Filed: Aug. 24, 2006

(65) Prior Publication Data

US 2007/0054415 A1 Mar. 8, 2007

(30) Foreign Application Priority Data

Sep. 2, 2005 (JP) .............................. 2005-255013

(51) Int. Cl.
*G01N 21/00* (2006.01)
*G01N 21/01* (2006.01)
*G01N 21/17* (2006.01)
*G01N 21/31* (2006.01)
*G01N 21/47* (2006.01)
*G01N 21/75* (2006.01)
*G01N 33/53* (2006.01)

(52) U.S. Cl. ............................ 436/164; 422/50; 422/52; 422/57; 422/68.1; 422/82.05; 422/100; 435/4; 435/7.1; 435/287.1; 435/287.2; 435/288.7; 436/501; 436/165; 436/166; 356/300

(58) Field of Classification Search ................ 435/287.2
See application file for complete search history.

(56) References Cited

U.S. PATENT DOCUMENTS 5,599,668 A * 2/1997 Stimpson et al. ................ 435/6

6,218,112 B1 * 4/2001 Thatcher et al. ................ 435/6
7,037,727 B1 * 5/2006 Miura et al. ................ 436/518
2002/0080358 A1 * 6/2002 Shimizu ..................... 356/445

(Continued)

FOREIGN PATENT DOCUMENTS

JP 02-242161 A 9/1990

(Continued)

OTHER PUBLICATIONS

Adama et al., Detection of hormone mimics in water using a miniturised SPR sensor, 2001 Env Mon and Assess 70: pp. 83-92.*

(Continued)

*Primary Examiner*—Unsu Jung
(74) *Attorney, Agent, or Firm*—Sughrue Mion, PLLC

(57) ABSTRACT

A surface plasmon resonance (SPR) assay apparatus is provided, in which a flow channel, a sensing surface and an optical assay unit are used. The sensing surface is associated with the flow channel, and contacted by a sample in the flow channel. The optical assay unit applies illuminating light to the sensing surface in contact with the sample, and measures reaction of the sample according to the illuminating light being reflected. A fluid dispenser, after measuring the reaction of the binding, introduces washing fluid on the sensing surface to wash the sensing surface. A cleanliness evaluator, according to the assay signal in the washing, checks whether a regenerated state of the sensing surface is such that the sensing surface is regenerated to an initial state prior to the reaction of the binding. A controller ends up the washing if the sensing surface has been regenerated to the initial state.

14 Claims, 12 Drawing Sheets

U.S. PATENT DOCUMENTS

2005/0158850 A1* 7/2005 Kubo et al. .............. 435/287.2

FOREIGN PATENT DOCUMENTS

| JP | 2661017 B2 | 10/1997 |
| JP | 2001-099805 A | 4/2001 |
| JP | 2002-131319 A | 5/2002 |
| JP | 2002-310903 A | 10/2002 |
| JP | 2003-194822 A | 7/2003 |

OTHER PUBLICATIONS

JP Notification of Reasons for Refusal, dated May 19, 2010, issued in corresponding JP Application No. 2005-255013, 9 pages in English and Japanese.

* cited by examiner

METHOD AND APPARATUS FOR ASSAY IN UTILIZING ATTENUATED TOTAL REFLECTION

BACKGROUND OF THE INVENTION

1. Field of the Invention

The present invention relates to a method and apparatus for assay in utilizing attenuated total reflection. More particularly, the present invention relates to a method and apparatus for assay in utilizing attenuated total reflection in which a sensing surface in a flow channel can be washed sufficiently and rapidly.

2. Description Related to the Prior Art

An assay apparatus for assay in utilizing attenuated total reflection is used for various kinds of studies in a biochemical field or the like, for example to study interaction of protein, DNA and various biomaterials, and to select candidate drugs by screening. Also, the technique is useful in the fields of the clinical medicine, food industries and the like.

A surface plasmon resonance (SPR) sensor is known as an assay apparatus in utilizing attenuated total reflection. A thin film/dielectric interface of a metal film is fitted on a dielectric block. Light is directed to the thin film/dielectric interface in a manner conditioned for total reflection. Surface plasmon is a term to mean the compressional wave created on the surface of the metal and included in plasmon as quantized expression of the compressional wave. Free electrons in a metal vibrate to generate the compressional wave.

The assay apparatus includes a light source device and a photo detector. The light source device emits light beams to the interface in the sensor unit at plural incident angles to satisfy the total reflection condition. The photo detector receives the reflected light from the interface, and detects intensity of the reflected light. The sensor unit has the thin film of metal. In the assay apparatus, surface plasmon resonance (SPR) is generated on the sensing surface. Reaction or interaction of a sample is assayed by measuring the surface plasmon resonance. An example of this is disclosed in JP-A 2002-310903.

Illuminating light is applied to an interface between the thin film and the prism or a surface back to the sensing surface at an angle of incidence equal to or more than a critical angle to satisfy a condition of total reflection. Then total reflection of the illuminating light occurs. Upon the total reflection created on the metal/dielectric interface, a small component of the light passes through the metal film without reflection, and penetrates to the sensing surface. A wave of the penetrating component is called an evanescent wave. Surface plasmon resonance (SPR) is created when frequency of the evanescent wave coincides with that of the surface plasmon. In response to this, intensity of the reflected light attenuates remarkably. In the assay apparatus, the attenuation in the reflected light reflected by the metal/dielectric interface is detected, to recognize creation of the SPR on the sensing surface. Intensity of the reflected light incident at an incident angle or resonance angle for creating the SPR is attenuated, so as to form a dark line on a photo reception surface.

A resonance angle or an angle of incidence of light for creation of surface plasmon resonance depends upon a refractive index of a medium of transmission of evanescent waves and surface plasmon. In other words, a change in the refractive index of the medium of transmission causes a change in the resonance angle of creation of SPR. The substance or sample in contact with the sensing surface is the medium for transmitting the evanescent waves and surface plasmon. When binding, dissociation or other reaction occurs on the sensing surface between two molecules or samples, the resonance angle changes because of a change in the refractive index of the medium of transmission. The SPR assay apparatus finds the changes in the resonance angle, to assay the interaction between the molecules or samples.

An assay apparatus for assay in utilizing attenuated total reflection is used for various kinds of studies in a biochemical field or the like, for example to study interaction of protein, DNA and various biomaterials, and to select candidate drugs by screening. In the screening, a ligand is protein or biomaterial. An analyte is any one of plural drugs, and is caused to contact the ligand for the purpose of investigating interaction between those. Also, the technique is useful in the fields of the clinical medicine, food industries and the like.

In an assay step for measuring interaction, at first analyte fluid containing analyte is caused to flow on a sensing surface where ligand is immobilized. So the ligand is contacted by the analyte in the measurement. After this, liquid buffer is introduced to the sensing surface, to measure reaction of dissociation in which the analyte is dissociated from the ligand. An assay signal in the reaction is detected in a real time manner in the assay step, and is recorded as measuring data.

It is important to increase throughput or efficiency of the assay particularly for the purpose of assaying reaction of a great number of samples. A reaction speed varies between the samples. A first one of the samples with a high value of the reaction speed can be assayed for obtaining a result of reaction such as presence or existence of binding. A second one of the samples with a low value of the reaction speed will take considerable time for obtaining a result of reaction. If a measuring time between the start and end of the assay is kept unchanged between samples, the measuring time is excessively long for a first one of the samples of which the reaction speed is high. The measuring time is excessively short for a second one of the samples of which the reaction speed is low.

JP-A2002-310903 discloses an assay method in which an assay signal output by the assay is monitored, so as to determine the measuring time according to the signal. The measuring time can be adjusted and minimized according to the reaction speed and the samples, so as to increase the throughput or efficiency of the assay.

After the assay step, the sensing surface is washed and regenerated by a washing step for a predetermined washing time. Washing liquid or regenerant is introduced to the sensing surface to remove residual part of the analyte remaining on the sensing surface. The sensing surface being regenerated is used in the assay.

However, there is a shortcoming of the known method due to a constant value of the predetermined washing time for the sensing surface. Should the washing time be too short, the washing is incomplete. Part of the analyte remains on the sensing surface, and influences measuring data of next assay, to lower precision in the assay. Should the washing time be too long, the throughput or efficiency cannot be high.

SUMMARY OF THE INVENTION

In view of the foregoing problems, an object of the present invention is to provide a method and apparatus for assay in utilizing attenuated total reflection in which a sensing surface in a flow channel can be washed sufficiently and rapidly.

In order to achieve the above and other objects and advantages of this invention, an assay method of assay in utilizing attenuated total reflection is provided, in which a sensor unit is used and includes a thin film, having a sensing surface for immobilizing ligand thereon, and a transparent dielectric medium overlaid with the thin film, wherein illuminating light is applied to an interface defined between the thin film and the dielectric medium by satisfying a total reflection condition, and intensity of the illuminating light reflected by the interface is detected to acquire an assay signal representing an attenuation angle of the illuminating light, so as to measure reaction of binding between the ligand and analyte introduced on the sensing surface. The assay method comprises a step of, after measuring the reaction of the binding, washing the sensing surface by introducing washing fluid thereon. In a cleanliness evaluating step, according to the assay signal in the washing, it is checked whether a regenerated state of the sensing surface is such that the sensing surface is regenerated to an initial state prior to the reaction of the binding. Then the washing is ended up if the sensing surface has been regenerated to the initial state.

In the cleanliness evaluating step, a first assay signal representing the regenerated state of the sensing surface is compared with an initial assay signal representing an initial state of the sensing surface prior to the reaction of the binding. If the first assay signal becomes equal to the initial assay signal, it is determined that the sensing surface has been regenerated to the initial state.

The first assay signal is acquired upon lapse of a predetermined time after a start of the washing.

If the first assay signal is different from the initial assay signal, the washing is continued.

The washing is continued by introducing the washing fluid again on the sensing surface.

If the first assay signal is different from the initial assay signal, the controller obtains a difference between the first assay signal and the initial assay signal, and compares the difference with a predetermined value. If the difference is equal to or more than the predetermined value, then the washing is continued in a modified washing condition.

A type or density of the washing fluid is changed before being introduced again on the sensing surface.

Furthermore, the washing fluid is caused to flow turbulently on the sensing surface.

Furthermore, a step of introducing air into a flow channel having the sensing surface by succeeding to a droplet of the washing fluid, wherein the droplet of the washing fluid and the air are moved alternately to pass the sensing surface.

If the first assay signal is different from the initial assay signal, and if the first assay signal changes with time and has such a ratio of change as to estimate reach to the initial assay signal, then the sensing surface is left to stand for natural regeneration.

If the first assay signal is different from the initial assay signal, then error information is recorded in error information recording, and the washing is ended up.

The washing fluid is at least one of regenerant and liquid buffer.

The washing fluid is at least a selected one of solution of physiological salt, pure water, solution of chloric acid, formic acid, and surface active agent.

Also, an assay apparatus of assay in utilizing attenuated total reflection is provided, in which a sensor unit including a thin film, having a sensing surface for immobilizing ligand thereon, and a transparent dielectric medium overlaid with the thin film, a light source device for applying illuminating light to an interface defined between the thin film and the dielectric medium by satisfying a total reflection condition, a photo detector for detecting intensity of the illuminating light reflected by the interface, to acquire an assay signal representing an attenuation angle of the illuminating light, a fluid dispenser for dispensing analyte to the sensing surface through a flow channel disposed to have the sensing surface, and for causing the analyte to contact the ligand, and a data analyzer for analyzing and measuring reaction of binding between the analyte and the ligand according to the assay signal. In the assay apparatus, the fluid dispenser, after measuring the reaction of the binding, introduces washing fluid on the sensing surface to wash the sensing surface. A cleanliness evaluator, according to the assay signal in the washing, checks whether a regenerated state of the sensing surface is such that the sensing surface is regenerated to an initial state prior to the reaction of the binding. A controller ends up the washing if the sensing surface has been regenerated to the initial state.

The cleanliness evaluator compares a first assay signal representing the regenerated state of the sensing surface with an initial assay signal representing an initial state of the sensing surface prior to the reaction of the binding. If the first assay signal becomes equal to the initial assay signal, the controller determines that the sensing surface has been regenerated to the initial state.

The first assay signal is acquired upon lapse of a predetermined time after a start of the washing.

If the first assay signal is different from the initial assay signal, the controller continues the washing step.

If the first assay signal is different from the initial assay signal, and if the first assay signal changes with time and has such a ratio of change as to estimate reach to the initial assay signal, then the sensing surface is left to stand for natural regeneration.

Furthermore, an error information recorder, if the first assay signal is different from the initial assay signal, records error information. The washing is ended up after the error information is recorded.

If the first assay signal is different from the initial assay signal, the controller obtains a difference between the first assay signal and the initial assay signal, and compares the difference with a predetermined value. If the difference is equal to or more than the predetermined value, then the controller continues the washing in a modified washing condition.

In one aspect of the invention, a computer executable program for assay is provided, in which a flow channel, a sensing surface and an optical assay unit are used, the flow channel causing a sample to flow, the sensing surface, associated with the flow channel, and contacted by the sample in the flow channel, the optical assay unit for applying illuminating light to the sensing surface in contact with the sample, and for measuring reaction of the sample according to the illuminating light being reflected. The computer executable program includes a washing code for washing the sensing surface by introducing washing fluid in the flow channel. A cleanliness evaluating code is for, according to the assay signal in the washing, checking whether a regenerated state of the sensing surface is such that the sensing surface is regenerated to an initial state prior to the reaction of the binding. A controlling code is for ending up the washing if the sensing surface has been regenerated to the initial state.

In another aspect of the invention, a user interface for assay is provided, in which a flow channel, a sensing surface and an optical assay unit are used, the flow channel causing a sample to flow, the sensing surface, associated with the flow channel, and contacted by the sample in the flow channel, the optical assay unit for applying illuminating light to the sensing surface in contact with the sample, and for measuring reaction of the sample according to the illuminating light being reflected. The user interface includes a washing region for washing the sensing surface by introducing washing fluid in the flow channel. A cleanliness evaluating region is for, according to the assay signal in the washing, checking whether a regenerated state of the sensing surface is such that the sensing surface is regenerated to an initial state prior to the reaction of the binding. A controlling region is for ending up the washing if the sensing surface has been regenerated to the initial state.

BRIEF DESCRIPTION OF THE DRAWINGS

The above objects and advantages of the present invention will become more apparent from the following detailed description when read in connection with the accompanying drawings, in which:

FIG. 1A is a vertical section illustrating an initial phase of introduction of droplets of the washing fluid and air;

DETAILED DESCRIPTION OF THE PREFERRED EMBODIMENT(S) OF THE PRESENT INVENTION

Figure 1:
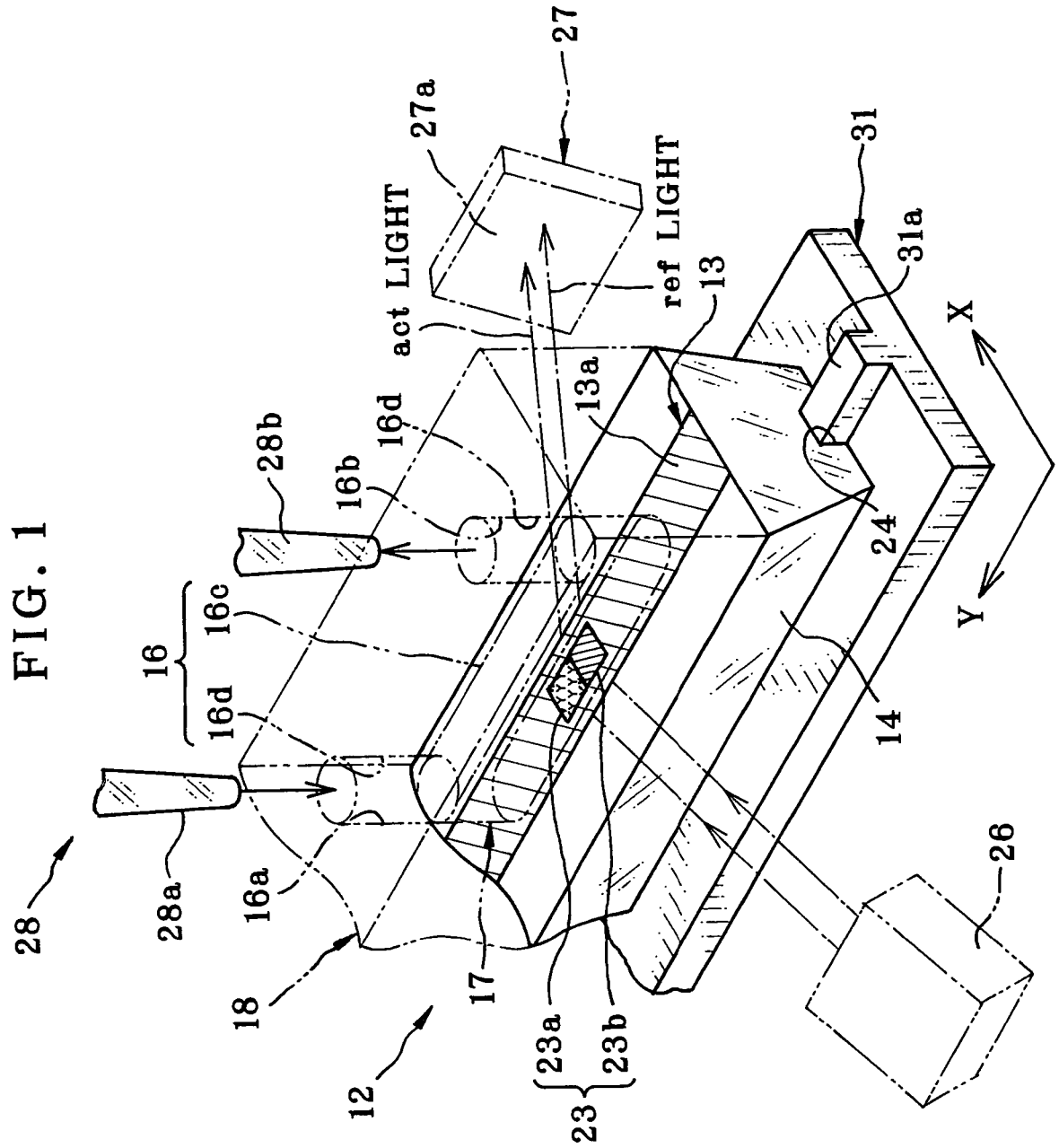
FIG. 1 is a perspective view illustrating an assay method.

In FIG. 1, a surface plasmon resonance (SPR) apparatus is provided with a sensor unit 12 for detecting association and/or dissociation between ligand and analyte. The assay apparatus includes an optical assay unit for detection, and a multi channel dispensing head or fluid dispenser 28 as two pipette devices 28a and 28b dispense or aspirate with a flow channel 16. The optical assay unit includes a light source device 26 and a photo detector 27. The light source device 26 emits light beams to the sensor unit 12 at plural incident angles to satisfy the total reflection condition. The photo detector 27 receives the reflected light from the sensor unit 12, and detects intensity of the reflected light. The photo detector 27 outputs an assay signal constituted by light intensity distribution on the photo reception surface. Reaction of the sample is measured by analyzing the assay signal according to changes in the resonance angle.

Figure 2:
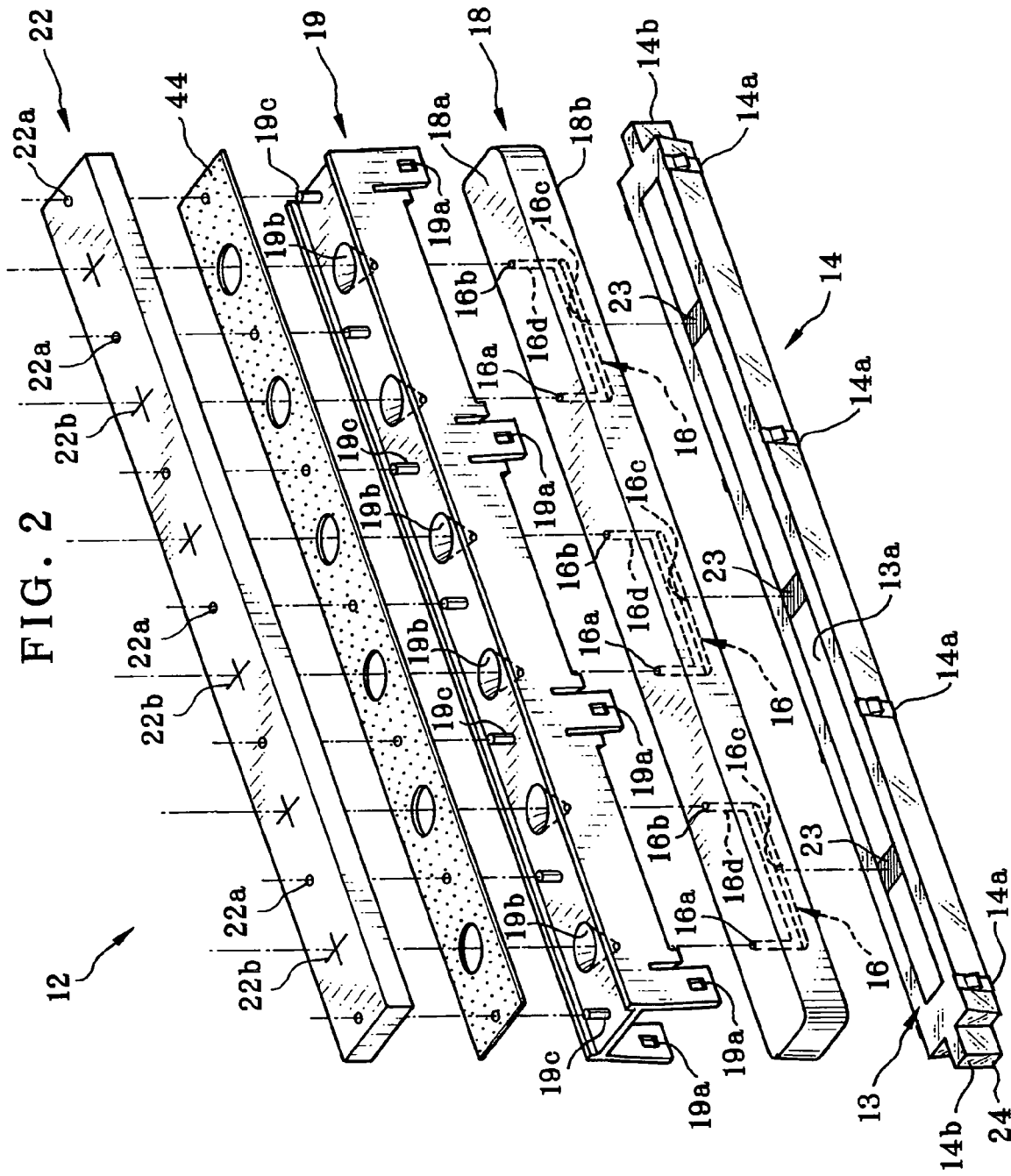
FIG. 2 is an exploded perspective view illustrating a sensor unit.

In FIG. 2, the sensor unit 12 includes a transparent prism 14 as a dielectric medium, a flow cell 18, a sealing block 19, and a flow cell lid 22. The flow cell 18 includes the flow channel 16 through which fluid flows. The sealing block 19 keeps the flow cell 18 pressed on an upper surface of the prism 14 to retain the flow cell 18. A double sided adhesive tape 21 attaches the flow cell lid 22 to the sealing block 19.

The flow cell 18 is in a prismatic shape of which a cross section is quadrilateral, and is formed from elastic material. A lower surface of the flow cell 18 is kept pressed on an upper surface of the prism 14. The flow channel 16 in an U shape includes a fluid passageway 16c and end cavities 16d. The fluid passageway 16c extends along the upper surface of the prism 14 and causes the fluid to flow on the prism 14. The end cavities 16d extend from each of ends of the fluid passageway 16c, and extend vertically to come through the flow cell 18 toward its upper surface 18a. First and second orifices 16a and 16b are open at upper ends of the end cavities 16d for insertion of pipette tips of the pipette devices 28a and 28b for dispensation and aspiration of sample fluid.

A horizontal width or diameter of the flow channels 16 is approximately 1 mm. An interval between the first and second orifices 16a and 16b of the flow channel 16 is approximately 10 mm. A lower side of the flow channels 16 where the fluid passageway 16c is open in the flow cell 18 is enclosed by the prism 14 having the sensing surface 13a. In the present embodiment, the sensor unit 12 has plural flow channels 16, for example three, arranged in the longitudinal direction of the flow cell 18.

A thin film 13 of metal is formed on the prism 14 by vapor deposition. A sensing surface 13a of the thin film 13 is directed upwards with reference to the prism 14. The thin film 13 is shaped in a strip form, and extends inside the flow channel 16 which is formed in the flow cell 18. Also, a linker film 23 or immobilization film is formed on the sensing surface 13a for immobilizing ligand. To produce the linker film 23, the linker film 23 is formed to overlie in the course of producing the sensor unit 12. A single one of sensor cells 17 is constituted by the sensing surface 13a having the linker film 23 and one of the flow channels 16.

In FIG. 1, there are a measuring region 23a (act) and a reference region 23b (ref) formed in the linker film 23. The measuring region 23a has immobilization of a ligand, and is a region for reaction between the ligand and sample. The reference region 23b does not have immobilization of a ligand, and is used for outputting a reference signal for comparison with a signal retrieved from the measuring region 23a. Note that the reference region 23b is formed in the course of film production of the linker film 23. An example of a process of the forming has steps of surface processing of the linker film 23 at first, and then deactivating the reaction groups in approximately a half of an entire area of the linker film 23 for binding with ligand. Thus, a half of the linker film 23 becomes the measuring region 23a. A remaining half of the linker film 23 becomes the reference region 23b.

At first, ligand fluid of ligand is introduced in the flow channel 16, so the ligand is immobilized on the measuring region 23a of the linker film 23. After the immobilization, analyte fluid of analyte is introduced in the flow channel 16, and contacts the ligand by flow to the linker film 23. An assay signal is output by detection, and analyzed for measuring binding reaction between the ligand and analyte.

The prism 14 is in a prismatic shape of which a cross section is trapezoidal. Various materials can be used for forming the prism 14, the examples including optical glasses, such as borosilicate crown (BK7) glass, barium crown (Bak4) glass, and the like; and optical plastic materials, such as polymethyl methacrylate (PMMA), polycarbonate (PC), amorphous polyolefin (APO) and the like.

The sealing block 19 keeps the prism 14 positioned on the flow cell 18. Plural retention tabs 19a are formed with the sealing block 19. Retention claws 14a are formed with lateral faces of the prism 14. The retention claws 14a are engaged with the retention tabs 19a for squeezing the flow cell 18 between the sealing block 19 and the prism 14. Positioning projections 14b project from ends of the prism 14 as viewed in the longitudinal direction. A sensor holder (not shown) for containing the sensor unit 12 has an inner surface, with which the positioning projections 14b are engaged for positioning the sensor unit 12.

A passage aperture 19b is formed in the sealing block 19. When the sealing block 19 is engaged with the prism 14 together with the flow cell 18, the first and second orifices 16a and 16b are connected with the passage aperture 19b. Rod shaped bosses 19c are formed to project from sides of the passage aperture 19b. Positioning holes 22a are formed in the flow cell lid 22, engaged with the bosses 19c for positioning the flow cell lid 22.

The flow cell lid 22 covers the passage aperture 19b communicating to the flow channel 16, and prevents evaporation of liquid in the flow channel 16. The flow cell lid 22 is formed from rubber, elastomer, resin or other elastic material. A cross shaped slit 22b is formed in the flow cell lid 22 and positioned respectively at the passage aperture 19b. The cross shaped slit 22b is formed to enable insertion of 28a and 28b, and to close the passage aperture 19b while no pipette is inserted. When the pipette devices 28a and 28b are externally pulled out, the cross shaped slit 22b elastically closes the passage aperture 19b again by returning to its initial state.

A bar code as information is printed on the sensor unit 12, and is constituted by information such as sensor ID of the sensor unit 12 for discernment of respective products. This makes it possible to manage data by associating results of assay of the sensor unit 12 with types of sample fluid being introduced. Note that an RFID tag (radio frequency identification tag) as a non-contact IC memory may be used with and secured to the sensor unit 12 in place of the bar code.

A table or assay stage 31 supports the sensor unit 12 in a removable manner. A handler (not shown) is installed, and shifts the sensor unit 12 from a standby position to the assay stage 31, to set the sensor unit 12 on the assay stage 31. A guide rail ridge 31a is formed on the assay stage 31 and engageable in a lower recess 24 in the sensor unit 12. The sensor unit 12 is slidable in a direction of extension of the guide rail ridge 31a. The sensor cells 17 are selectively set in the assay position by the sliding of the sensor unit 12. To slide the sensor unit 12, the handler operates to shift the sensor unit 12.

Figure 3:
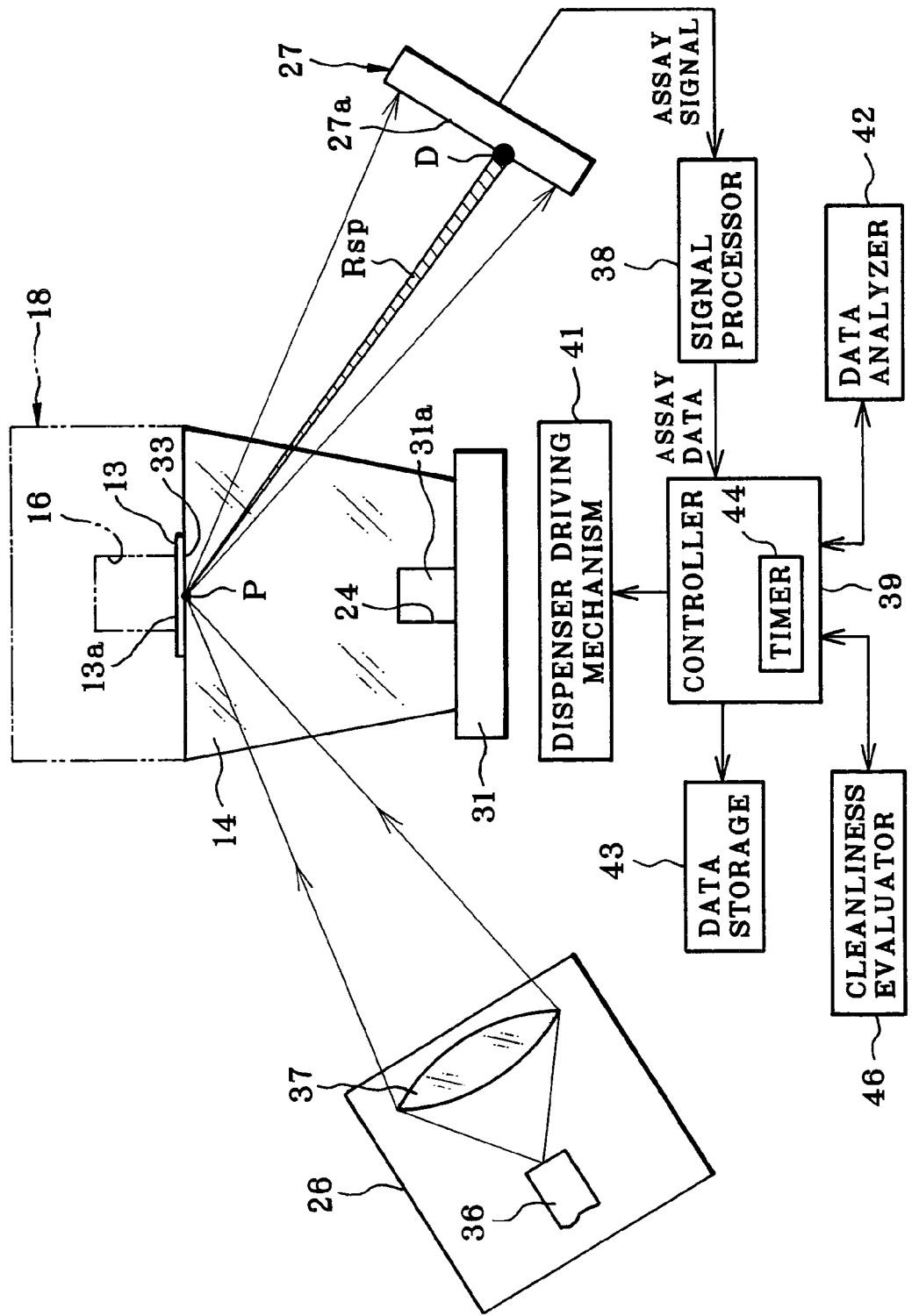
FIG. 3 is an explanatory view in an elevation and block diagram, illustrating an assay apparatus.

An interface 33 is defined between the prism 14 and the thin film 13. In FIG. 3, the light source device 26 emits light to the interface 33. As interaction between the ligand and analyte is detectable as changes in the resonance angle, the light source device 26 causes light beams of various incident angles to the interface 33 in the total reflection condition. The light source device 26 includes a light source and optical system. Examples of the light source device include a light emitting diode (LED), laser diode (LD), super luminescent diode (SLD), and other light emitting element.

The optical system includes a collimator lens, an optical fiber 36, and a condensing lens 37. Light passed through and exited from the optical fiber 36 is condensed by the condensing lens 37 and becomes incident upon a specific incident point on the interface 33 in a converged manner. Thus, light beams of various incident angles strike the interface 33. A position of incidence of the light beams is the measuring point P where light intensity of the reflected light is detected to obtain an assay signal. Also, light beams, which are applied to the measuring and reference regions 23a and 23b, are obtained by splitting light emitted by a single light source.

An example of the photo detector 27 is a CCD area sensor or an array of photo diodes. The photo detector 27 receives the light reflected on a measuring point P in the interface 33, converts the reflected light to output an SPR signal of levels according to the intensity of the light. At the measuring point P, the interface 33 reflects light beams incident at various angles of incidence. The reflected light at various angles of reflection becomes incident on the photo detector 27. The photo detector 27 outputs signals of light intensity of reflected light having various reflection angles. Thus, a distribution of light intensity of the reflected light is obtained.

Figure 4:
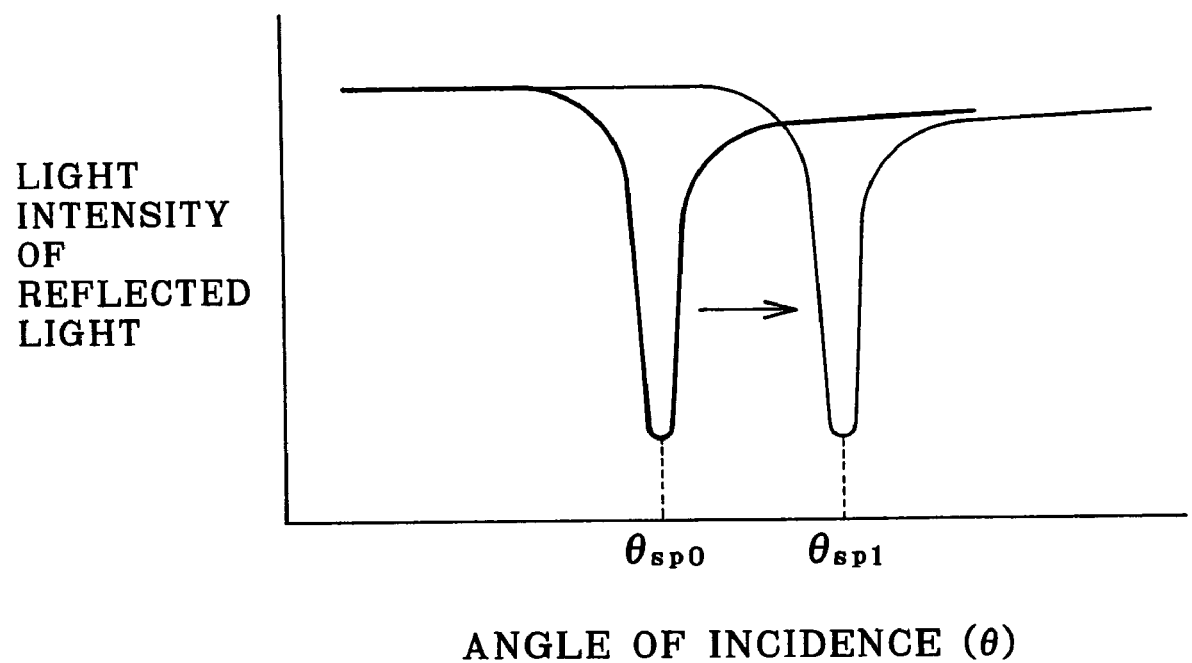
FIG. 4 is a graph illustrating a relationship between light intensity and a resonance angle.

A resonance angle to produce surface plasmon resonance is determined according to a refractive index of a medium in contact with the thin film 13. In the graph of FIG. 4, there occurs considerable attenuation of light intensity of reflected light Rsp (hatched in FIG. 3) upon incidence at a resonance angle θsp within light beams of incident angles θ. A photo reception surface 27a of the photo detector 27 detects a reception position D or dark line position of the reflected light Rsp. In the graph of FIG. 4, the refractive index is changed by reaction between the ligand and analyte. This changes the resonance angle θsp from θsp0 to θsp1, to shift the dark line position D on the photo reception surface 27a. The reaction of binding between the ligand and analyte is assayed by acquiring changes in the dark line position D according to the assay signal.

The photo detector 27 outputs an act-signal for the measuring region 23a, and a ref-signal for the reference region 23b. A signal processor 38 produces measuring data according to either a different or a ratio between the act signal and the ref signal. This makes it possible to cancel electric noise caused by external irregularities, such as individual specificity of the sensor unit or the sensor cells, mechanical changes of the assay apparatus, temperature changes of the liquid, and the like. The assay with high precision is possible.

A controller 39 controls various devices included in the assay apparatus, for example the multi channel dispensing head 28, the light source device 26 and the photo detector 27. A dispenser driving mechanism 41 drives the multi channel dispensing head 28. The controller 39 causes the dispenser driving mechanism 41 to drive the multi channel dispensing head 28 for aspiration and dispensation.

A data analyzer 42 analyzes the measuring data, and acquires changes of a resonance signal (SPR signal) with time, the resonance signal expressing an attenuation angle of the reflected light according to a resonance angle. The assay process includes a reaction measuring step and a washing step, the reaction measuring step measuring interaction between the analyte and ligand, the washing step regenerating the sensing surface 13a for next assay. The SPR signal is acquired for all of the period of the assay.

Figure 5:
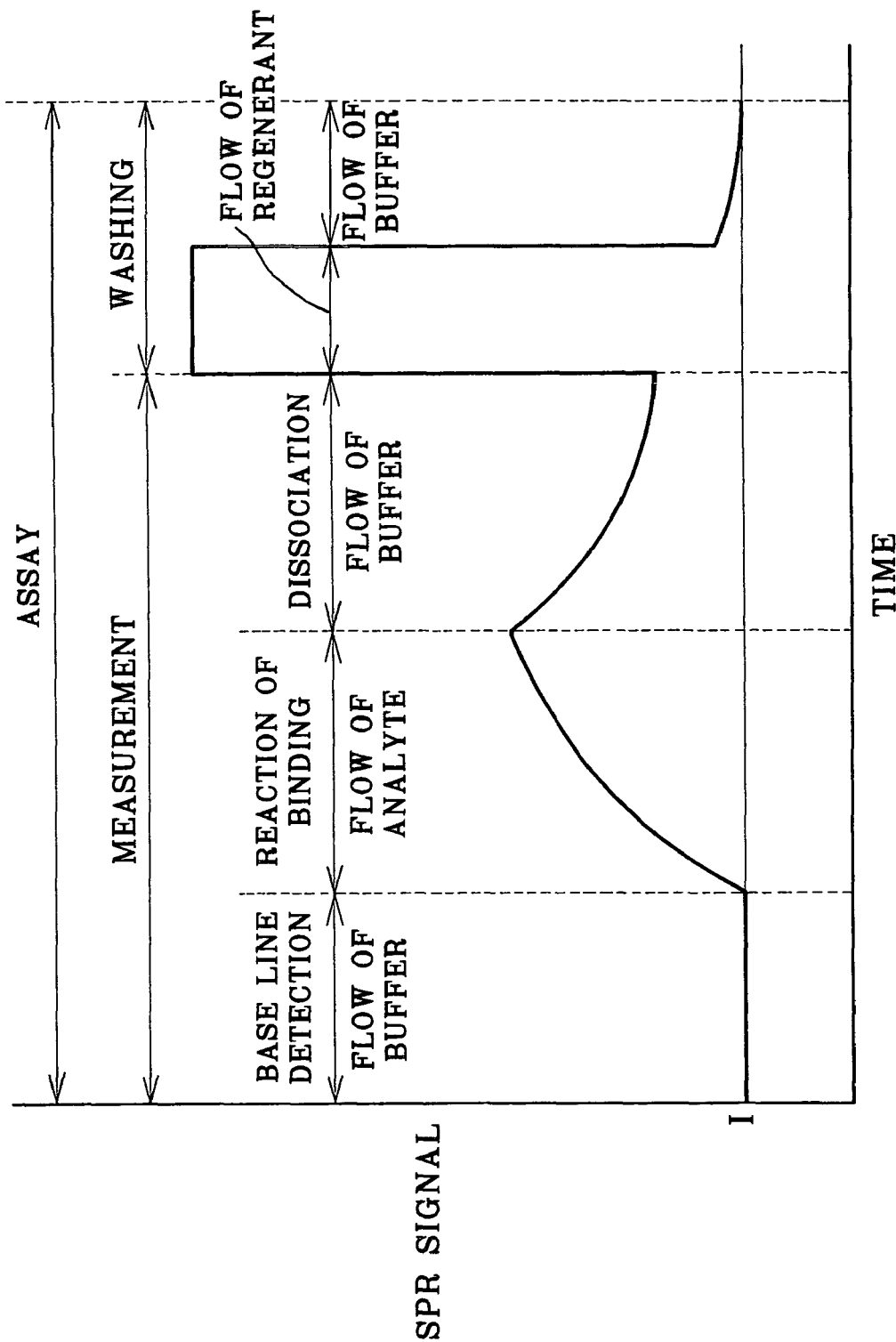
FIG. 5 is a graph illustrating changes of the SPR signal with time in the assay.

FIG. 5 is a graph indicating changes in the SPR signal with time in the total period of a single process of assay. The assay includes a reaction measuring step and a washing step. In the reaction measuring step, interaction between the ligand and analyte is assayed. In the washing step, the sensing surface 13a is washed or regenerated for next assay. In the reaction measuring step, at first the buffer is introduced to the sensing surface 13a, to output an SPR signal for a resonance angle according to a refractive index of the sensing surface 13a at this time. A level of the SPR signal upon introduction of the buffer is an initial level of the signal prior to the reaction measuring step for the binding. A base line or initial level I is obtained, and used as a reference for evaluating the binding reaction.

Then analyte fluid constituted by analyte and fluid medium is introduced to the sensing surface 13a, and is subjected to measurement of reaction of binding. When reaction of binding occurs on the sensing surface 13a between ligand and analyte, the refractive index changes to change the attenuation angle. Thus, a signal level of the SPR signal rises. After the measurement, the buffer liquid is introduced to the sensing surface 13a, to measure dissociation between the ligand and analyte. In response to the dissociation, a state of the sensing surface 13a comes near to an initial state prior to binding of the analyte with the ligand. A signal level of the SPR signal is lowered, and becomes near to the initial level I.

Various liquids are available for assay, and solvent or diluent for the analyte fluid, for example, liquid buffer, physiological saline water and other aqueous solutions of physiological salts, and pure water. It is possible according to a type of a ligand or analyte to determine suitably solution types and pH values of the solutions, and types of substances to be mixed, and their density.

When measurement of reaction is completed, the sensing surface 13a is washed. In the washing, washing fluid 50 (See FIGS. 10, 11A and 11B) is introduced to the sensing surface 13a to remove residual analyte. So the sensing surface 13a is regenerated for an initial state before the binding reaction, to prepare the sensing surface 13a for next assay. Examples of the washing fluid 50 used herein are a regenerant and a liquid buffer. The regenerant has such a characteristic as to remove the analyte from the sensing surface 13a, and also as to keep characteristics of the ligand without modification. Specific examples of regenerants are physiological saline water, solution of chloric acid, formic acid, surface active agent.

When the regenerant is introduced through the flow channel 16 to the sensing surface 13a, the refractive index is abruptly changed by the regenerant, to cause a level of the SPR signal to rise abruptly. The regenerant is kept stored in the flow channel 16, before the liquid buffer is introduced to the flow channel 16. The pressure of the liquid buffer causes the regenerant to exit from the flow channel 16, so as to lower the level of the SPR signal. Most of the residual analyte in the sensing surface 13a is exited together with the regenerant from the flow channel 16. However, a small part of the residual analyte remains in contact with the sensing surface 13a. The liquid buffer is introduced to apply pressure to and eliminate the residue of the regenerant with the residual analyte from the sensing surface 13a. While the liquid buffer is stored in the flow channel 16 for a predetermined time, the level of the SPR signal decreases according to a degree of washing. The number of times of introduction of the liquid buffer in the washing is three. Note that the number of times of introduction of the liquid buffer in the washing may be one or two, or four or more, and can be determined according to the amount and types of samples.

A data storage 43 stores changes in the SPR signal with time as a result of the assay. A timer 44 measures elapsed time. A cleanliness evaluator 46 determines the regenerated state of the sensing surface 13a according to the SPR signal during the washing. The controller 39 is responsive to a result output by the cleanliness evaluator 46, and determines whether the washing should be ended or continued.

Figure 6:
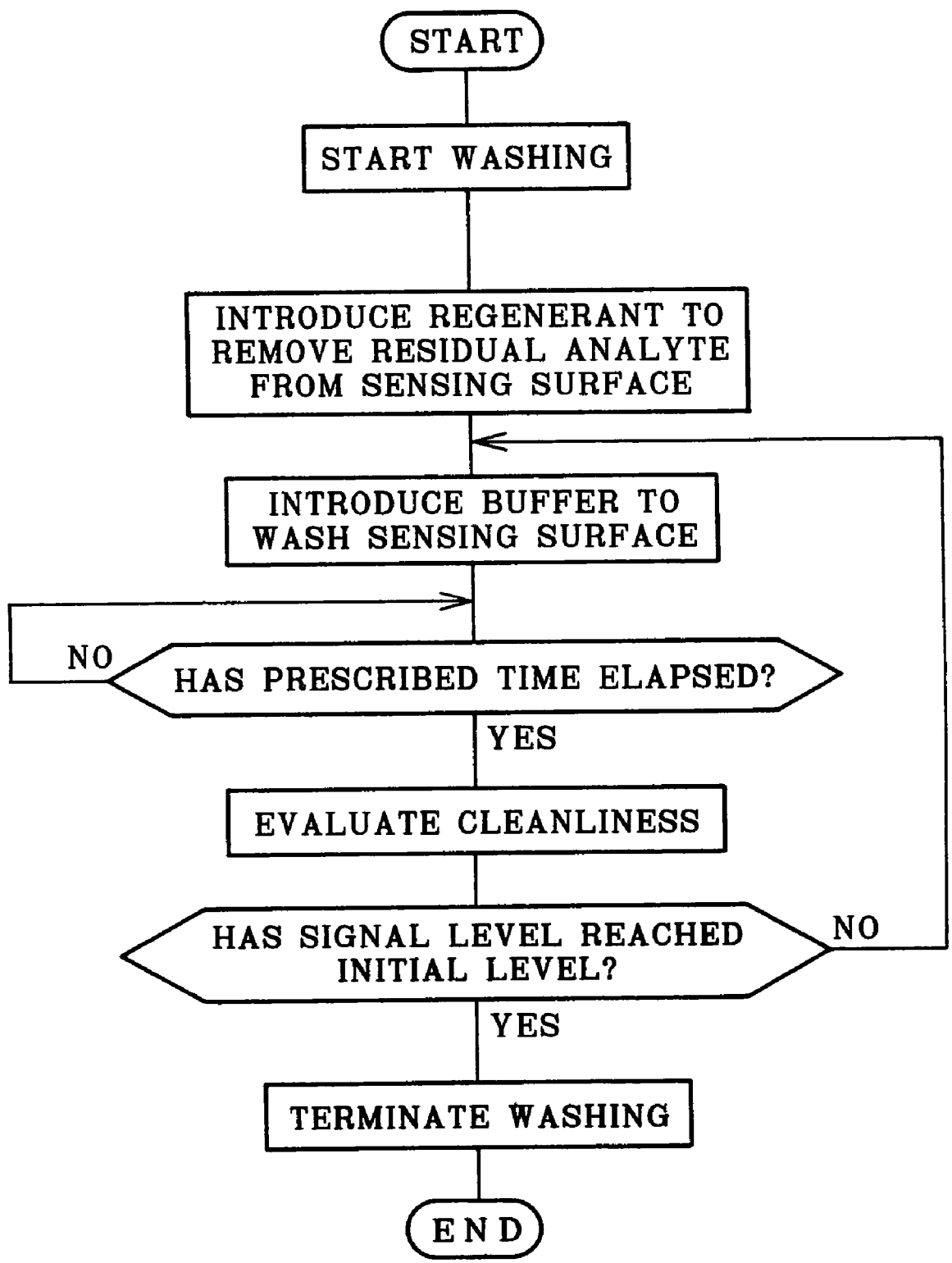
FIG. 6 is a flow chart illustrating washing.

In FIG. 6, a flow of washing is illustrated. When washing is started, regenerant and liquid buffer as the washing fluid 50 are introduced into the flow channel 16. When a predetermined time elapses after starting introducing the washing fluid 50, then a cleanliness evaluating step is started. The cleanliness evaluator 46 checks whether a level of the SPR signal has come down to the initial level I. If it has, then a state of the sensing surface 13a is detected to have come back to the initial state by regeneration.

The controller 39, upon receiving a result of finding the regeneration to the initial state, comes to operate for ending the washing. The controller 39 causes the multi channel dispensing head 28 to remove buffer liquid from the flow channel 16, to complete the washing.

If the level of the SPR signal has come down to the initial level I, then the cleanliness evaluator 46 determines that the state of the sensing surface 13a has not been regenerated to the initial state. In response to this, the controller 39 determines continuation of the washing. Then the controller 39 causes the multi channel dispensing head 28 to introduce liquid buffer again to the flow channel 16, for flow to the sensing surface 13a. Again, the regenerated state of the sensing surface 13a is estimated, to determine completion or continuation of the washing. This is repeated for one or more times until the regenerated state comes back to the initial state.

The SPR signal is monitored during the washing, to check the regenerated state of the sensing surface 13a. When the sensing surface 13a is regenerated by washing to the initial state again, the washing is terminated. Waste time for washing can be saved due to continued washing despite the regeneration to the initial state. Decrease in throughput of the assay can be prevented. As a result of detecting the regenerated state, the washing continues if the sensing surface 13a has not been regenerated to the initial state. Thus, no residual sample after the assay remains on the sensing surface 13a. Next assay can be free from an incompletely regenerated state. Reaction of the sample can be measured precisely.

In the above embodiment, only the liquid buffer is used for introduction at the second time of washing in continuation. However, it is possible to introduce both of the regenerant and liquid buffer for the second time of washing. In FIG. 6, a flow of introduction of regenerant and liquid buffer is illustrated. The liquid buffer is introduced after the regenerant.

Figure 7:
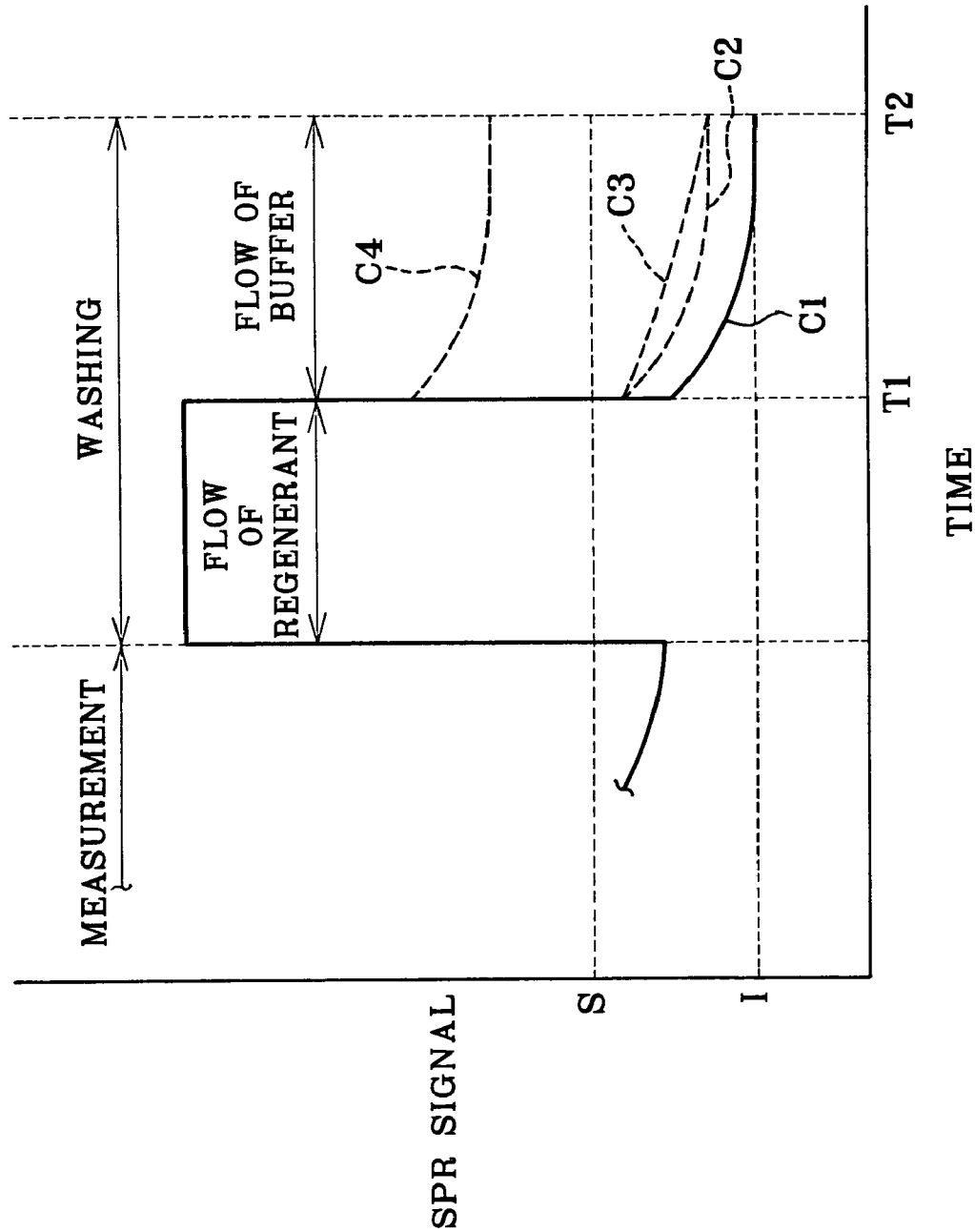
FIG. 7 is a graph illustrating changes of the SPR signal with time in the washing.

In the above embodiment, the method of washing is the same even when the washing is continued. However, the degree of the progress of the washing of the sensing surface considerably varies according to the type and amount of the sample upon lapse of a predetermined time after starting the washing. In FIG. 7, curves C1-C4 are depicted to express changes of the SPR signal with time until lapse of predetermined time after the start of washing. According to this, it is possible to check the regenerated state inclusive of the progress of the washing as well as the regeneration of the sensing surface to the initial state.

In the curve C1, a signal level decreases toward the initial level from the time T1 of starting introduction of the liquid buffer, and comes down to the initial level I at the time T2. In the curves C2-C4, a signal level does not come down to the initial level I at the time T2. Thus, the sensing surface 13a has not been regenerated to the initial state because of the incomplete washing. Among the curves C2-C4, the curves C2 and C3 are shaped with a higher level of the signal than the initial level I, but with a lower level than the predetermined value S. The curve C4 is shaped with a higher level than the predetermined value S. It is possible in the cleanliness evaluator 46 to analyze those curves to check the regenerated state, so as to change a parameter or characteristic of the washing according to the result.

Figure 8:
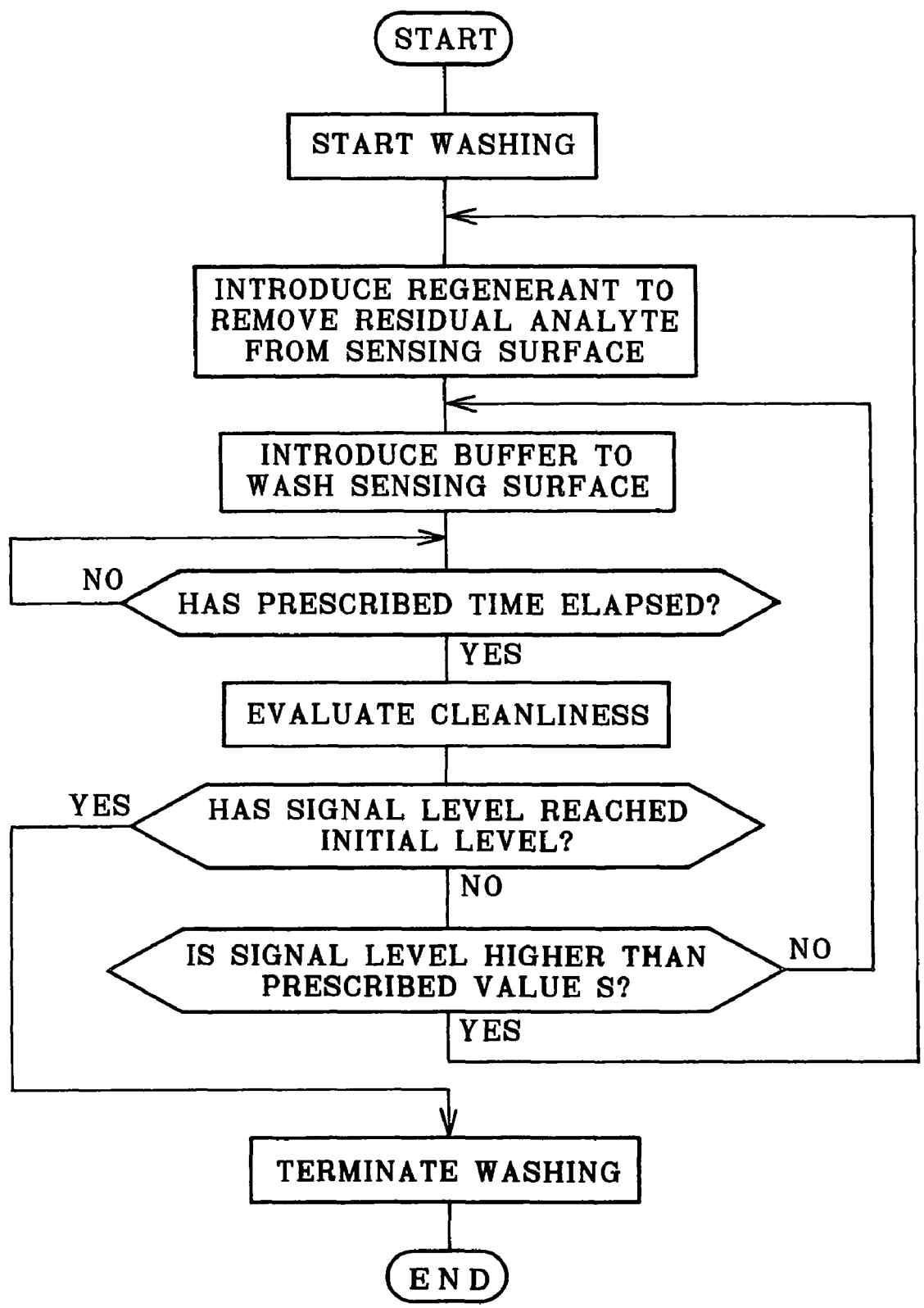
FIG. 8 is a flow chart illustrating one preferred washing process of which portions are changed according to a signal level in comparison with a predetermined value.

In a flow chart of FIG. 8, at first it is checked whether the signal level has reached the initial level I in the cleanliness evaluation. If the signal level has reached the initial level in the form of the curve C1, the washing is ended because the sensing surface has been regenerated to an initial state. If the signal level has not reached the initial level I in the form of the curves C2, C3 and C4, the washing is continued but in a modified form. At least one parameter or characteristic of the washing is modified or changed in the modified form according to whether a difference between the signal level and the initial level I is equal to or more than a predetermined amount. In the case of the curve C4 with a level over the value S that is higher than the initial level I, it is estimated that washing proceeds considerably slowly. Thus, washing is executed again by introduction of the regenerant liquid, to introduce the regenerant liquid and the buffer. In the case of the curves C2 and C3 with a level under the value S, the washing proceeds more rapidly than the case of the curve C4. Only the buffer liquid is caused to flow, without use of the regenerant liquid.

Figure 9:
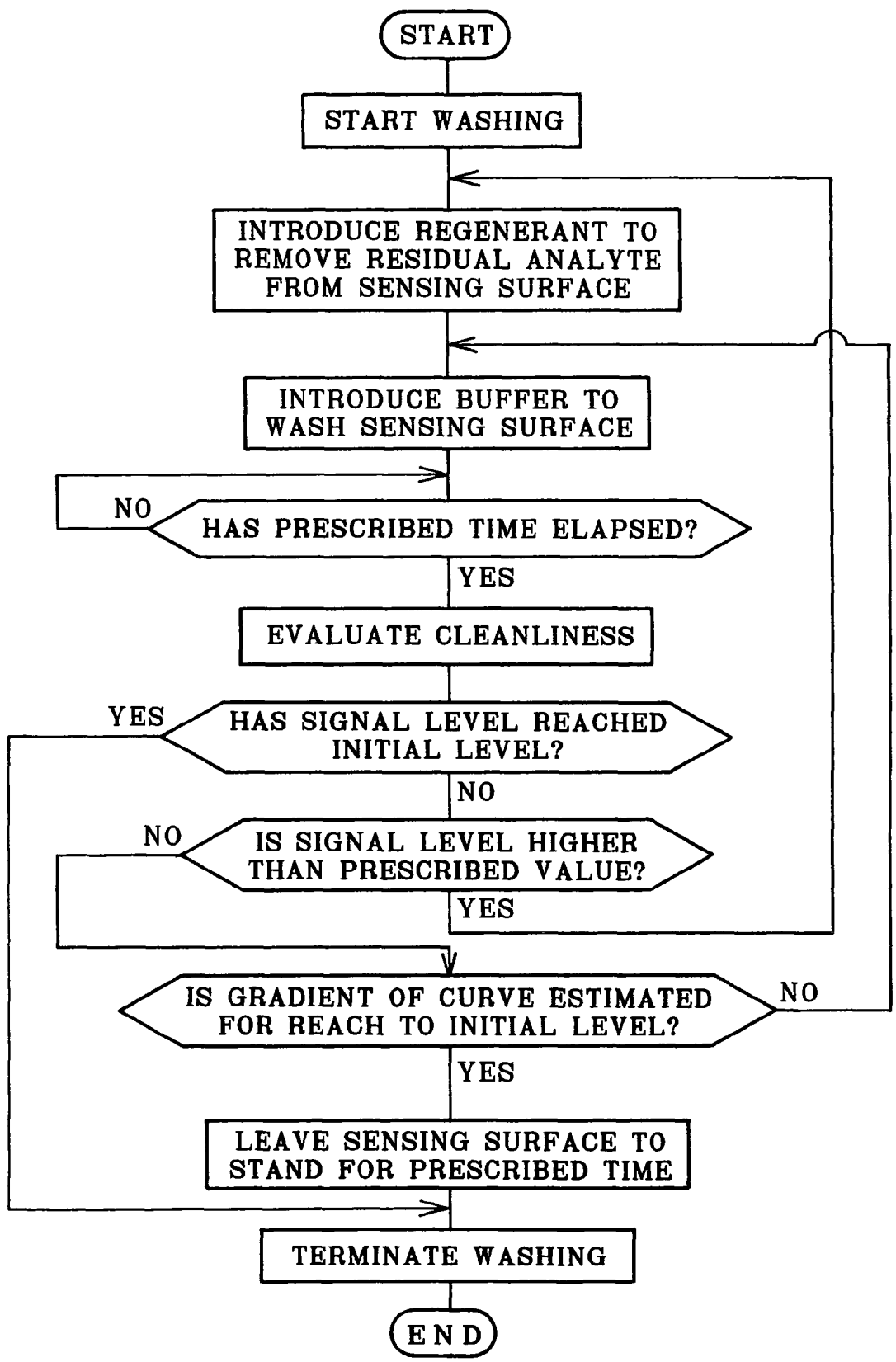
FIG. 9 is a flow chart illustrating one preferred washing process of which portions are modified according to a gradient of a curve of the SPR signal.

According to the curves C2 and C3, the signal level at the time T2 is equal. However, a gradient is different between those. In the curve C2, no change in the signal level is observable because of the horizontal form without a gradient. In contrast, the curve C3 is inclined toward the initial level I. Possibility in further decrease in the signal level according to the curve C3 is expected. Thus, a standby step of FIG. 9 can be additionally used. If a curve is found to have a gradient to direct toward the initial level I in the manner of the curve C3, the liquid buffer may be stored in the flow channel 16 for a predetermined time, and left to stand for the purpose of standby for a natural decrease of the signal level at the end of the washing.

Figure 10:
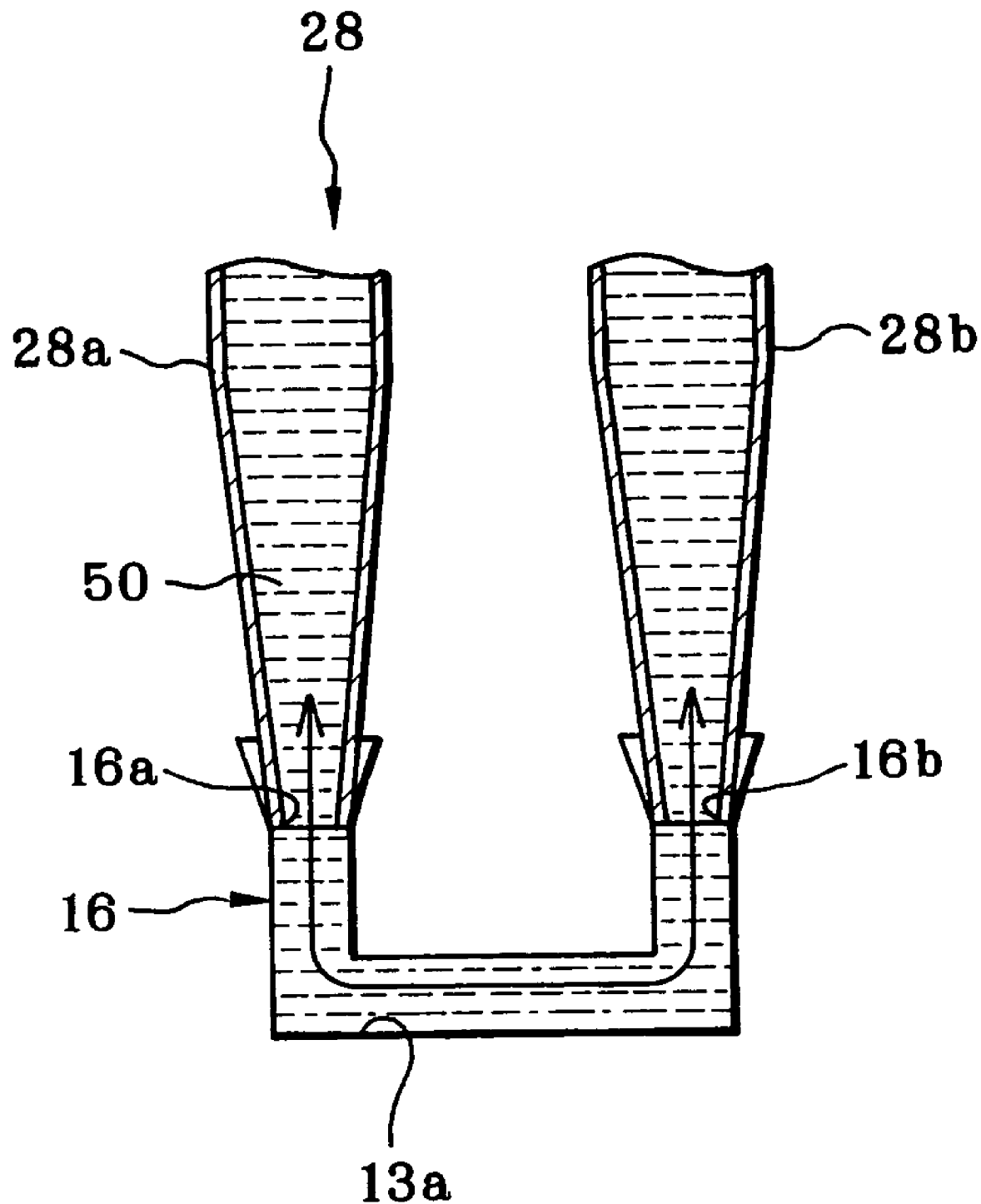
FIG. 10 is a vertical section illustrating a method of a turbulent flow of the washing fluid.

In FIG. 10, one preferred embodiment is illustrated, in which the washing fluid 50 is stirred or caused to flow turbulently by the multi channel dispensing head 28 to fluidize the washing fluid 50 in contact with the sensing surface 13a upon repeated introduction of the washing fluid 50 into the flow channel 16. A first one of the pipette devices 28a and 28b in the multi channel dispensing head 28 dispenses the washing fluid 50, which a second one of those aspirates the washing fluid 50. The dispensation and aspiration are alternated so that the washing fluid 50 can be stirred or caused to flow turbulently within the flow channel 16. Cleaning power for the sensing surface 13a can be increased in comparison with simple introduction of the washing fluid 50 to the flow channel 16. Increase in the cleaning power is also effective in shortening time required for washing. This is specifically effective in the situation of the curve C4 in which the degree of the progress of the washing is considerably small on the sensing surface 13a.

Figure 11A:
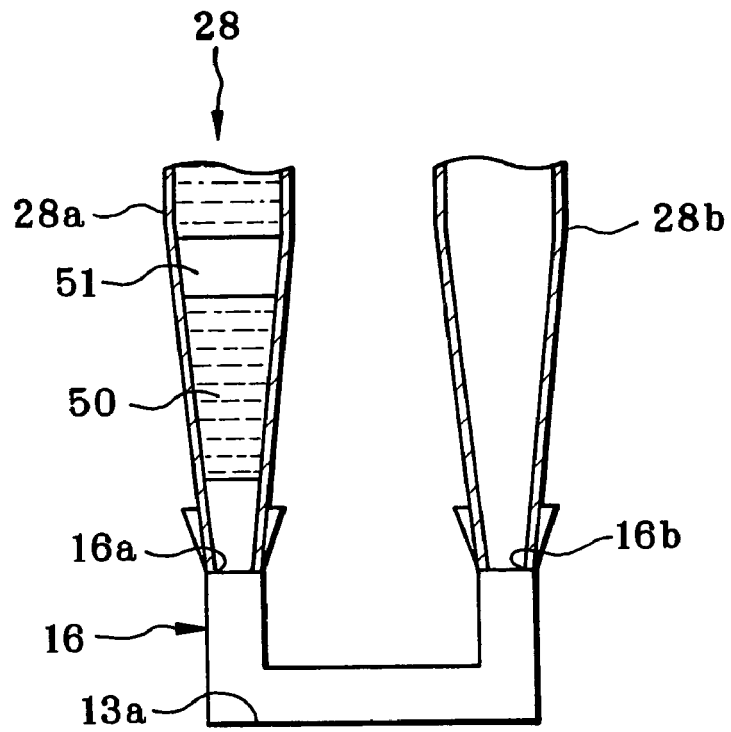
FIG. 11B is a vertical section illustrating a second phase of the same as FIG. 11A.
Figure 11B:
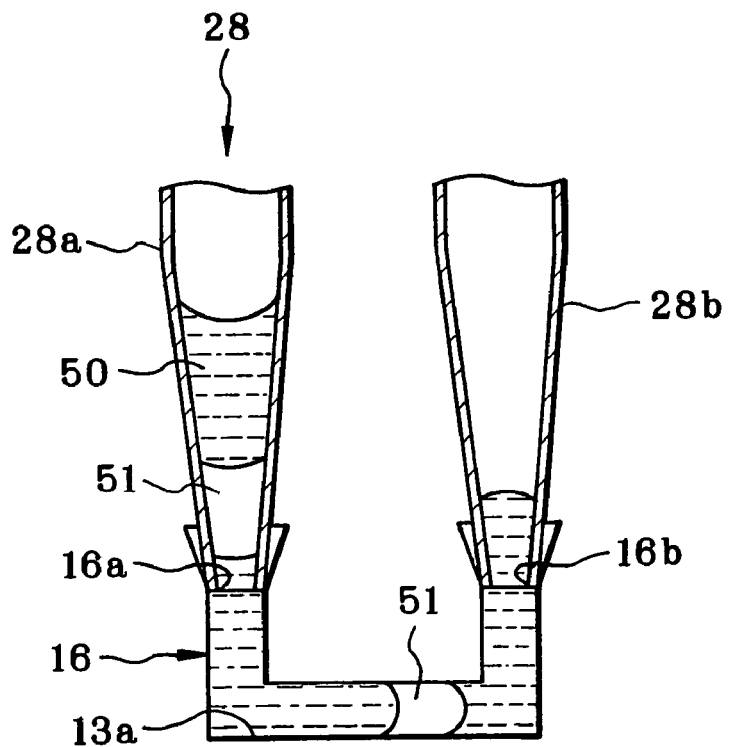

In FIGS. 11A and 11B, use of air 51 in combination with the washing fluid 50 is illustrated. The air 51 is introduced through the flow channel 16 toward the sensing surface 13a together with the washing fluid 50. For this construction, at first the first pipette device 28a of FIG. 11A aspirates droplets of the washing fluid 50 and the air 51 in an alternate manner. In FIG. 11B, the first pipette device 28a dispenses and introduces the washing fluid 50 and the air 51 alternately. Those pass the sensing surface 13a in the alternate form of the droplets of the washing fluid 50 and the air 51 through the flow channel 16. Furthermore, the washing fluid 50 and the air 51 can be stirred or caused to flow turbulently in the flow channel 16 according to the process of FIG. 10. Higher effect of washing can be obtained.

It is possible to use a second type of the washing fluid 50 different from the first type of the washing fluid 50 in the composition or density, so as to introduce the second type as a second washing step. This is effective in raising effects of washing. Furthermore, the stirring and/or alternate introduction of air may be combined with the change of the washing fluid 50 in the composition or density.

Figure 12:
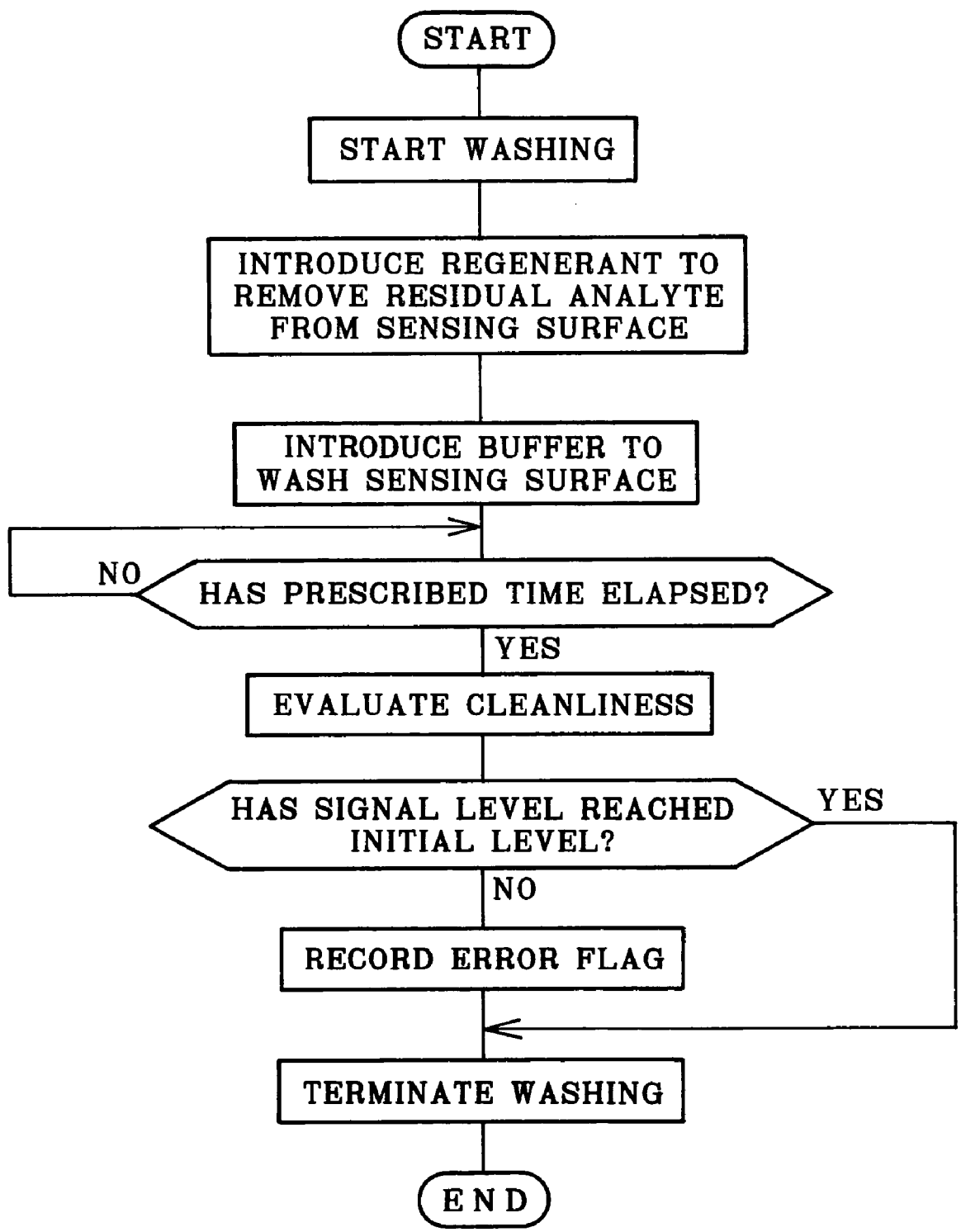
FIG. 12 is a flow chart illustrating a washing process in which an error flag is recorded when washing is incomplete.

In FIG. 12, another preferred embodiment with an error flag is illustrated. In the above embodiment, continuation of washing is scheduled after incomplete washing. In contrast, if the signal level has not come down to the initial level I, an error flag recording step is added to record the error flag which is a result of determining incompleteness of the washing. The washing may be completed without continuation. The error flag is written by the controller 39 as error information recorder to the data storage 43 in relation to the ID information for specifically determining the particular sensing surface 13a. An example of ID information includes sensor unit ID information, and channel ID information associated with a specified one of sensor cells in the sensor unit. Recording to the error flag makes it possible to discern a particular one of the sensing surface 13a of which washing is incomplete. The particular sensing surface 13a can be kept from being used in next assay, and if used incidentally next, can be eliminated from consideration in relation of a result of the assay.

The use of the error flag is specifically effective in the multi channel sensor unit having the plural flow channels, as the washing is forcibly ended according to writing of the error flag when the washing is incomplete. If simultaneous assay for plural flow channels is desired, a first one of the flow channels may take long time for being washed. The remaining flow channels other than the first must wait for the complete washing of the first, which will decrease the throughput of the assay. Even when the washing is insufficient for one of the flow channels, waiting time for remaining flow channels can be minimized by recording an error flag for the first flow channel to start next assay step. Thus, throughput of the assay can be kept high without dropping.

The plural preferred embodiments have been described. Also, a composite embodiment is preferable in combination of continuation of the washing and recording of an error flag. To this end, the level of the SPR signal is checked in comparison with a certain reference level. If the level is equal to or more than the reference level, then the recording or the error flag is used. In contrast, if the level is equal to or less than the reference level, then the washing is continued as a second time.

There are two examples of patterns of continuing the washing, including repeated introduction of the washing fluid 50, standby of the washing fluid 50 for a predetermined time, or the like. Plural examples of the repeated introduction are conceivable, including stirring, changing or the density of the washing fluid 50. In the above embodiment, two or more of the possible patterns are combined specifically. Also, other combinations are possible. In the case of the curve C4, an error flag can be set and recorded in a storage. In the case of the curve C3, the flow channel is left to stand for a predetermined time. In the case of the curve C2, the washing fluid 50 is introduced again. Among those, any two or more of specific examples may be used in combination.

The sensor unit 12 disclosed herein is a multi channel type having the three flow channels, but may be a modified type having only one flow channel, or a multi channel type having two or four or more flow channels.

In the above embodiments, the sensor unit 12 is a component including the thin film, the flow channel and the prism. However, it is possible for the assay apparatus to include a prism or flow cell, which may not be included in the sensor unit.

In addition to the SPR sensor, an assay sensor unit according to the invention can be other sensor in utilizing attenuated total reflection. One example of sensor unit according to utilizing the attenuated total reflection is a leaky mode sensor. The leaky mode sensor includes a dielectric medium, a cladding layer overlaid on the dielectric medium, and an optical waveguide layer overlaid on the cladding layer, those layers constituting a thin film. A first surface of the thin film is a sensing surface on the optical waveguide layer. A second surface of the thin film is a metal/dielectric interface on the cladding layer. When light becomes incident on the metal/dielectric interface to satisfy the condition of the total reflection, part of the light passes through the cladding layer, and enters the optical waveguide layer. A guided mode to propagate light is excited responsively in the optical waveguide layer, to attenuate the reflected light on the metal/dielectric interface. An angle of the incidence at which the guided mode is excited is changeable according to the refractive index of the medium positioned on the sensing surface. This is similar to the characteristic of the resonance angle of the SPR sensor. The attenuation of the reflected light is detected, so that it possible to measure the interaction on the sensing surface.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An assay method of assay in utilizing attenuated total reflection, in which a sensor unit is used and includes a thin film, having a sensing surface for immobilizing ligand thereon, and a transparent dielectric medium overlaid with said thin film, wherein illuminating light is applied to an interface defined between said thin film and said dielectric medium by satisfying a total reflection condition, and intensity of said illuminating light reflected by said interface is detected to acquire an assay signal representing an attenuation angle of said illuminating light, so as to measure reaction of binding between said ligand and analyte introduced on said sensing surface, said assay method comprising steps of:

after measuring said reaction of said binding, washing said sensing surface by introducing washing fluid thereon;

according to said assay signal in said washing, checking a regenerated state of said sensing surface;

determining whether said sensing surface is regenerated to an initial state prior to said reaction of said binding or not; and ending up said washing if it is determined in said determining step that said sensing surface has been regenerated to said initial state, wherein in said checking step, a first assay signal representing said regenerated state of said sensing surface is compared with an initial assay signal representing said initial state of said sensing surface prior to said reaction of said binding; and if a level of said first assay signal reaches a level of said initial assay signal, it is determined that said sensing surface has been regenerated to said initial state in said determining step, and wherein if it is determined that said sensing surface has not been regenerated to said initial state in said determining step said, washing continues with only liquid buffer in a first state where the level of said first assay signal is not higher than a predetermined value, and wherein said washing continues with liquid buffer and a regenerant in a second state where the level of said first assay signal is higher than said predetermined value.

2. An assay method as defined in claim 1, wherein said first assay signal is acquired upon lapse of a predetermined time after a start of said washing.

3. An assay method as defined in claim 1, wherein if said first assay signal is different from said initial assay signal, said washing is continued.

4. An assay method as defined in claim 3, wherein said washing is continued by introducing said washing fluid again on said sensing surface.

5. An assay method as defined in claim 3, wherein if said first assay signal is different from said initial assay signal, said controller obtains a difference between said first assay signal and said initial assay signal, and compares said difference with a predetermined value;

if said difference is equal to or more than said predetermined value, then said washing is continued in a modified washing condition.

6. An assay method as defined in claim 5, wherein a type or density of said washing fluid is changed before being introduced again on said sensing surface.

7. An assay method as defined in claim 5, further comprising a step of causing said washing fluid to flow turbulently on said sensing surface.

8. An assay method as defined in claim 5, further comprising a step of introducing air into a flow channel having said sensing surface by succeeding to a droplet of said washing fluid, wherein said droplet of said washing fluid and said air are moved alternately to pass said sensing surface.

9. An assay method as defined in claim 1, wherein if said first assay signal is different from said initial assay signal, and if said first assay signal changes with time and has such a ratio of change as to estimate reach to said initial assay signal, then said sensing surface is left to stand for natural regeneration.

10. An assay method as defined in claim 1, wherein said washing fluid is at least one of regenerant and liquid buffer.

11. An assay method as defined in claim 1, wherein said washing fluid is at least a selected one of solution of physiological salt, pure water, solution of chloric acid, formic acid, and surface active agent.

12. An assay method as defined in claim 1, wherein if said first assay signal is different from said initial assay signal, and if said first assay signal changes with time and does not have such a ratio of change as to estimate reach to said initial assay signal, then liquid buffer is added to wash the sensing surface to aid in regeneration.

13. An assay method as defined in claim 1, wherein said first assay signal is calculated based on intensity of reflected light from an interface received by a photo detector according to light pattern attenuation.

14. An assay method as defined in claim 1, wherein the assay signal is a result of surface plasmon resonance.

* * * * *